United States Patent [19]

DesRosiers

[11] Patent Number: 5,674,119
[45] Date of Patent: *Oct. 7, 1997

[54] HAND HELD DENTAL SAW

[76] Inventor: Marc DesRosiers, 10,239 Boulevard Gouin, Montreal, Quebec, Canada, H1C 1A2

[*] Notice: The term of this patent shall not extend beyond the expiration date of Pat. No. 5,529,532.

[21] Appl. No.: 666,004

[22] Filed: Jun. 19, 1996

Related U.S. Application Data

[63] Continuation-in-part of Ser. No. 507,777, Jul. 26, 1995, Pat. No. 5,529,532.

[51] Int. Cl.⁶ .............. B24B 23/00; B24B 27/08
[52] U.S. Cl. .................. 451/344; 451/456
[58] Field of Search .............. 451/344, 456, 451/388; 83/100; 30/276, 340

[56] References Cited

U.S. PATENT DOCUMENTS

| | | |
|---|---|---|
| 1,763,730 | 6/1930 | Von Lackum . |
| 2,344,262 | 3/1944 | Odierna et al. . |
| 2,490,255 | 12/1949 | Chase . |
| 2,815,050 | 12/1957 | Haug . |
| 2,972,363 | 2/1961 | Santilli . |
| 3,688,403 | 9/1972 | Bettcher . |
| 3,799,021 | 3/1974 | Hammerschlag . |
| 4,022,182 | 5/1977 | Lenkevich . |
| 4,316,328 | 2/1982 | Duggan et al. . |
| 4,361,957 | 12/1982 | Krotz et al. .............. 83/100 |
| 4,363,170 | 12/1982 | McCullough . |
| 4,472,880 | 9/1984 | Johansson . |
| 4,494,311 | 1/1985 | McCullough . |
| 4,555,849 | 12/1985 | Ando et al. .............. 30/388 |
| 4,575,938 | 3/1986 | McCullough . |
| 4,589,208 | 5/1986 | Iwasaki et al. .............. 30/376 |
| 4,637,140 | 1/1987 | Bettcher . |
| 4,646,607 | 3/1987 | Johansson . |
| 4,790,225 | 12/1988 | Moody et al. .............. 83/100 |
| 4,827,617 | 5/1989 | Shepherd . |
| 4,972,588 | 11/1990 | Briach, Sr. .............. 30/388 |
| 5,020,226 | 6/1991 | Chabbert . |
| 5,084,976 | 2/1992 | Ross . |
| 5,230,154 | 7/1993 | Decker et al. . |
| 5,239,783 | 8/1993 | Matechuk .............. 451/456 |
| 5,531,639 | 7/1996 | Catalfamo .............. 451/456 |

FOREIGN PATENT DOCUMENTS

| | | |
|---|---|---|
| 476783 | 4/1948 | Canada . |
| 626285 | 8/1961 | Canada . |
| 759277 | 5/1967 | Canada . |

*Primary Examiner*—James G. Smith
*Assistant Examiner*—Derris H. Banks
*Attorney, Agent, or Firm*—Theresa Fritz Camoriano; Wheat Camoriano Smith & Beres

[57] ABSTRACT

A miniature motorized hand held dental saw wherein the axis of rotation of the handle of the dental saw is tangent to the cutting edge of the blade. This important characteristic, combined with the use of a flexible blade, enables the operator to change, as needed, the direction of the cut without any snagging or binding effects. The dental saw preferably includes a main steel body on which are attached three flanged Teflon™ coated bearings that support and guide a thin, annular blade. The rotation of the blade, on these flanged bearings, is created by a drive assembly including two opposite wheels, a drive wheel and a follower wheel, each wheel including a hub on which is fitted an o-ring. The opposite o-rings create an equal pressure on both faces of the blade and cause the blade to rotate.

14 Claims, 8 Drawing Sheets

HAND HELD DENTAL SAW

BACKGROUND-FIELD OF THE INVENTION

This is a continuation-in-part of U.S. patent application Ser. No. 08/507,777, filed Jul. 26, 1995 now Pat. No. 5,529,532. This invention relates to saws, and, in particular, to a small, motorized, hand-held saw which may be used for sawing dental casts and other workpieces.

Many motorized, hand-held saws are known, but they are generally difficult to handle. These known saws are not useful for intricate cutting, such as for cutting dental casts, because they are heavy and cannot readily turn tight corners as required. Also, many motorized saws create vibrations which can crack and ruin a dental cast.

Hand-operated coping saws are known, but, because the sawing action is done by hand, the saw cannot cut very quickly, and the person operating the saw may become tired and may have difficulty keeping the saw on the correct path while moving it back and forth to create the sawing action.

None of the known saws provide a motorized annular saw designed to duplicate the motion of a hand held-coping saw, which is widely used around the world, while allowing as much control on the tilting of the tool during cutting as when using the manual coping saw, and while permitting increased speed, maneuverability, and longer lasting blades.

SUMMARY OF THE INVENTION

The present invention solves many of the problems of the prior art by providing a motorized saw which has the maneuverability of a coping saw while being able to operate at increased speed and increased accuracy.

In the preferred embodiment, the increased maneuverability is achieved by making the axis of rotation of the handle tangent to the cutting edge of the blade, the blade being flexible, to allow the operator to modify the course of the cut, thus permitting the blade to change direction during the cut.

The portion of the cutting edge which is tangent to the axis of the handle is the portion that does the cutting, so that a rotation of the handle by 1° about its axis also creates a rotation of the cutting edge of 1° about the axis of the handle, thereby providing excellent control by the operator of the saw.

The preferred embodiment also provides a vacuum tube which extends through the handle of the saw and terminates adjacent to the blade, so that the tube can vacuum up dust particles that are created when the saw cuts into a workpiece.

A power source is remote and flexibly connected to the saw. The power source is an electric motor connected to a torsion cable mounted in a flexible sheath. The torsion cable drives the drive wheel, which drives the cutting blade.

The blade is preferably mounted on a set of three flanged guide bearings in contact with the inner edge of the blade, two of the flanged guide bearings having each a fixed central axis and having between each other a cutting area to permit passage of a workpiece, the third flanged guide bearing being mounted on a spring arm located on the fore end and being biased towards the inner edge of the blade.

The means for controlling the speed of rotation of the blade preferably is a pressure switch, which, by means of electrical lines extending through the sheath, provides a variable speed control for the motor which drives the blade.

DESCRIPTION OF A PREFERRED EMBODIMENT

An embodiment of the invention is described in the following figures where the same characterizing elements are identified by the same numbers.

Figure 1:
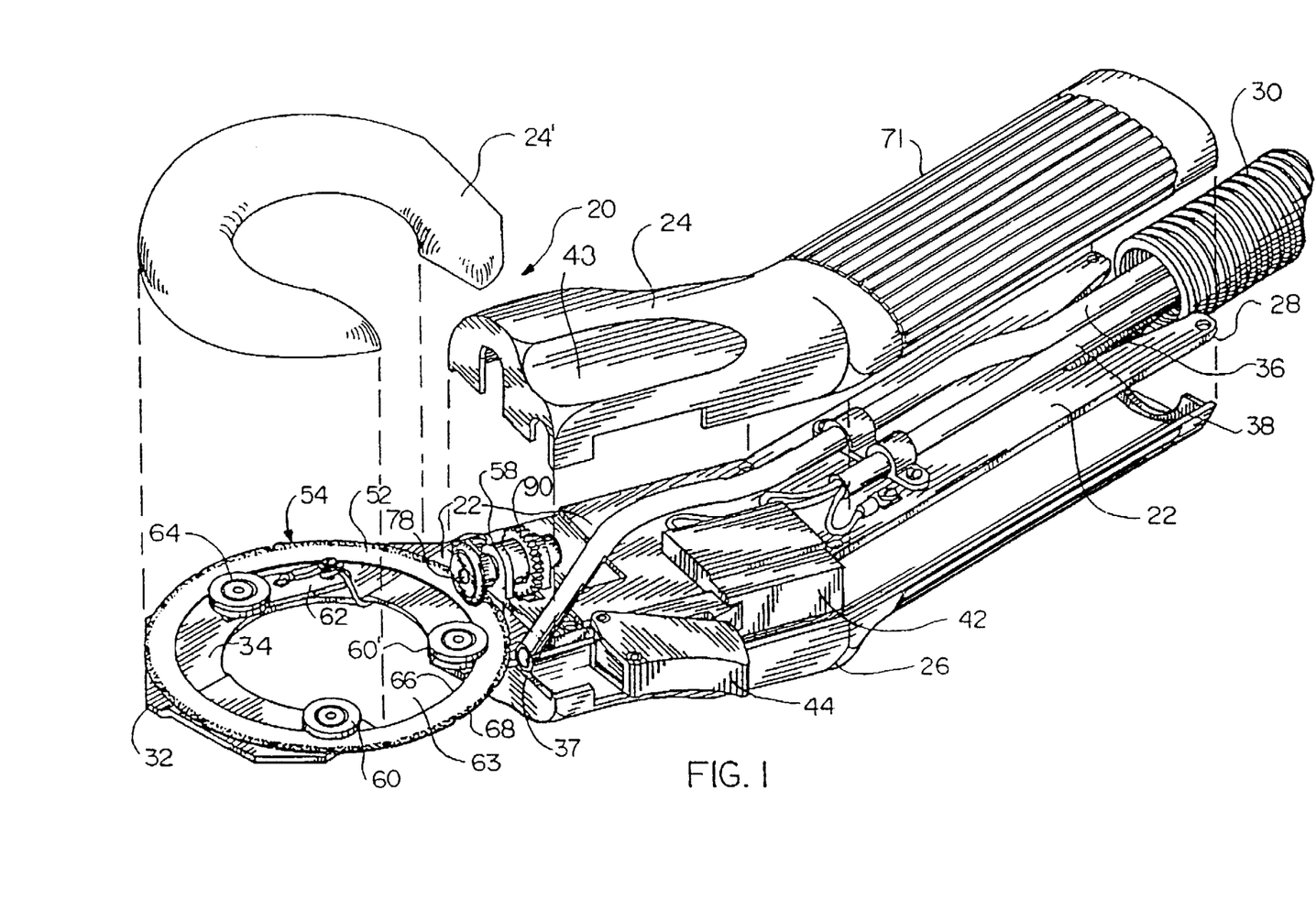
FIG. 1 is an exploded perspective view of a preferred embodiment of a saw made in accordance with the present invention.

FIG. 1 shows a miniature annular hand held dental saw 20, which includes a main body 22, which is sandwiched in between a left outer shell portion 24 and a right outer shell portion 26, which shell portions together form a grip 71. The left and right outer shell portions and main body 22 are preferably held together by screws (not shown). The main body 22 holds, at an aft end 28, a conduit 30 and, at a fore end 32, an arched support 34. The conduit 30 encloses a vacuum tube 36, which terminates at an aspiration opening 37, adjacent to the cutting edge of the saw 20. The conduit 30 also encloses an electrical cable 38 and a drive cable 40, which appears in FIG. 2.

The electrical cable 38 leads to a variable speed control 42, which is located on the main body 22, and which is equipped with a finger plunger or button 44, which projects out of the shell portions 24, 26. There is a recess 43 on the left outer shell portion 24 for receiving the thumb of a right-handed person, as shown in FIG. 8. The case may be made with a similar recess on the right outer shell portion 26 for use by a left-handed person, although that is not shown here. When the operator pushes the button 44, he controls the variable speed control 42, mounted on the main body 22, which transmits a signal through the electrical cable 38 to provide variable speed control to a motor 46 (FIG. 7B), which rotates the drive cable 40.

Figure 4A:
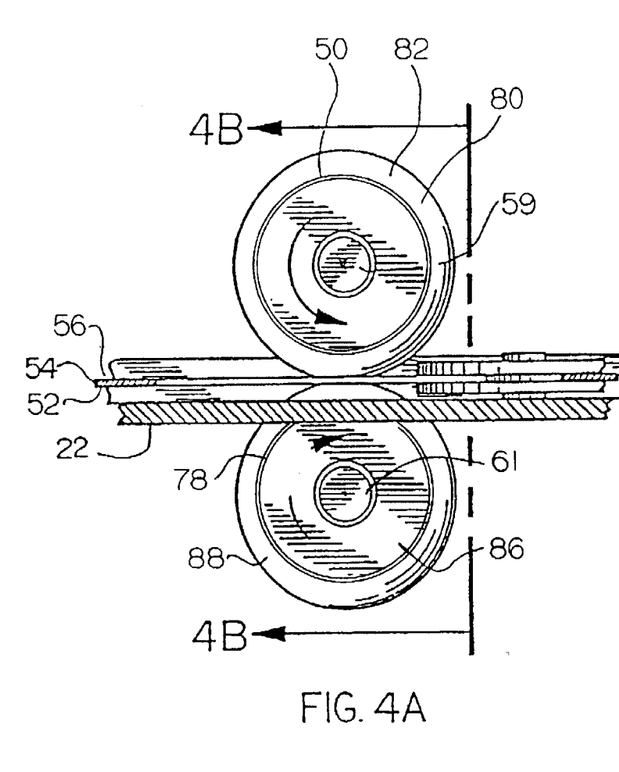
FIG. 4A is a view taken along the section 4A—4A of FIG. 2.
Figure 4B:
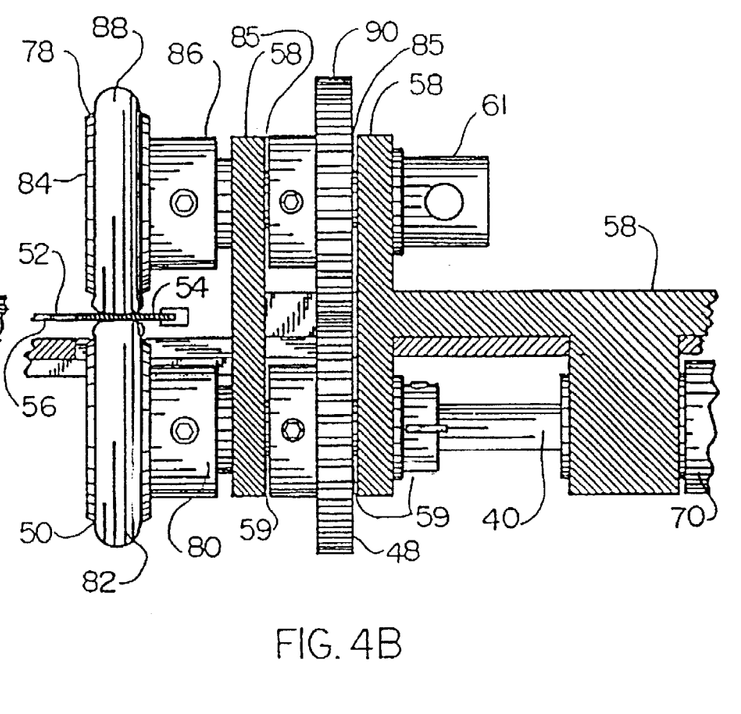
FIG. 4B is a view taken along the section 4B—4B of FIG. 2.

As shown in FIG. 4B, the drive cable 40, in turn, drives a primary shaft 59, which drives a nylon gear 48 and coaxially transmits power to a drive wheel 50, which engages the right face 56 of an annular diamond flexible blade 54. A drive assembly 58 supports the secondary shaft 61, which drives the follower wheel 84. The secondary shaft 61 is driven by the gear 90, which is driven by the gear 48.

The arched support 34 (FIG. 1) supports two fixed flanged guide bearings 60. The arched support 34 defines a gap 63, which defines the cutting area, with the two fixed flanged guide bearings 60 located at the edges of the gap 63. The arched support 34 also supports a third flanged guide bearing 64, fixed to a mobile spring loaded tension arm 62. The third, movable guide bearing 64 is located opposite the gap 63, as shown, so that the axes of the three guide bearings 60, 64 lie at the three points of an equilateral triangle. The two fixed flanged guide bearings 60 and the third flanged guide bearing 64 all contact the inner edge 66 of the blade 54. The outer edge 68 of the blade 54 is the cutting edge of the blade 54.

Figure 2:
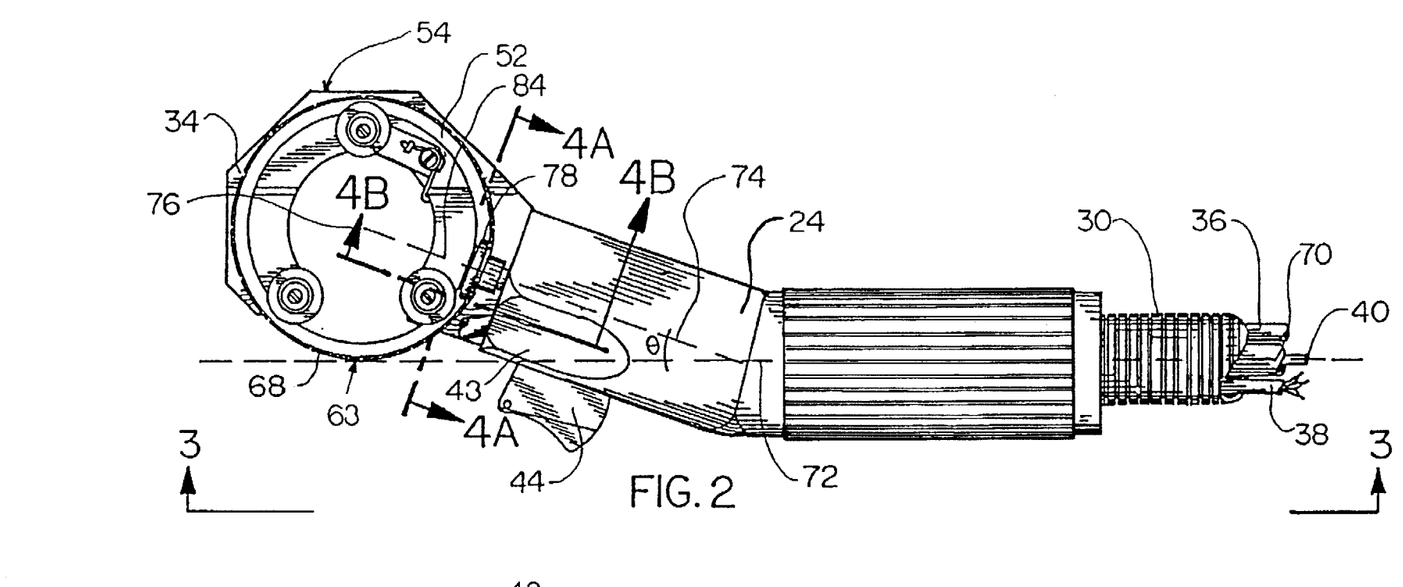
FIG. 2 is a left side view of the saw of FIG. 1, with part of the sheath broken away.

At FIG. 2, one can see a view of the left outer shell portion 24 and the finger plunger 44 in position ready to be pressed for controlling the speed of rotation of the drive wheel 50. The drive cable 40, vacuum tube 36, and electrical cable 38 are inside the conduit 30. The drive cable 40 is inside the sheath 70, which extends through the grip 71. The grip portion 71 of the shell 24, 26 has an axis of rotation 72 (FIG. 2). The left and right shell portions 24, 26 then extend at an angle to the grip portion 71 of the handle along an axis 74, which is parallel to the axis of the shaft 59 of the drive wheel 50 and parallel to a follower axis 84 of a follower wheel 78, the axis 74 continuing to the center 76 of the annular flexible blade 54. The intersection of the extension axis 74 and the handle rotation axis 72 forms an angle 8. For best results, it is desirable that the angle θ be such that the continuation of the axis of rotation 72 of the grip 71 coincides with a tangent of a circle formed by the outer edge 68 of the annular blade 54 in the cutting area 63, so that the portion of the blade 54 which cuts a workpiece is tangent to the axis of rotation 72 of the grip portion 71 of the handle.

Figure 3:
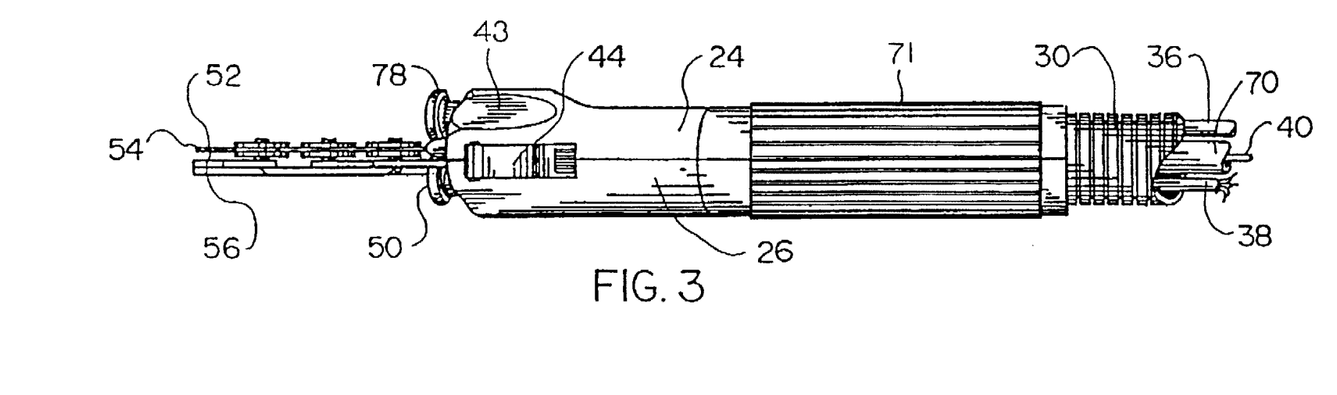
FIG. 3 is a bottom view taken along the line 3—3 of FIG. 2.

At FIG. 3, one can see the drive wheel 50 acting against the right face 56 of the annular blade 54. Opposed to the drive wheel 50 is the follower wheel 78 acting against the left face 52 of the blade 54. The vacuum tube 36, drive cable 40, and the electrical cable 38 appear in the same relative position with respect to the sheath 70.

At FIG. 4A, one can see the drive wheel 50 turning counter-clockwise along with its primary shaft 59, the drive wheel 50 comprising two parts, namely a hub 80, preferably made of brass, and an o-ring 82, preferably made of neoprene, which surrounds the hub 80. It is the o-ring 82 which rests against the right face 56 of the blade 54 and drives the blade 54 as the hub 80 rotates. Facing the drive wheel 50 is a follower wheel 78 with a follower shaft 61 and a follower brass hub 86 surrounded by a neoprene follower o-ring 88, which frictionally engages the left face 52 of the annular flexible blade 54.

At FIG. 4B, one can see the drive cable 40 driving the drive shaft 59, which drives the drive gear 48 and at the same time drives the drive wheel 50 and the drive o-ring 82, which frictionally engages the right face 56 and drives the blade 54. The drive gear 48 engages a similar follower nylon gear 90, which turns a follower shaft 61, which turns the follower wheel 78 and its o-ring 88, which frictionally engages the left face 52 of the blade 54 in a clockwise direction, so that the blade 54 is actually driven by the two wheels 50, 78, pressing against opposite sides of the blade 54.

Figure 5A:
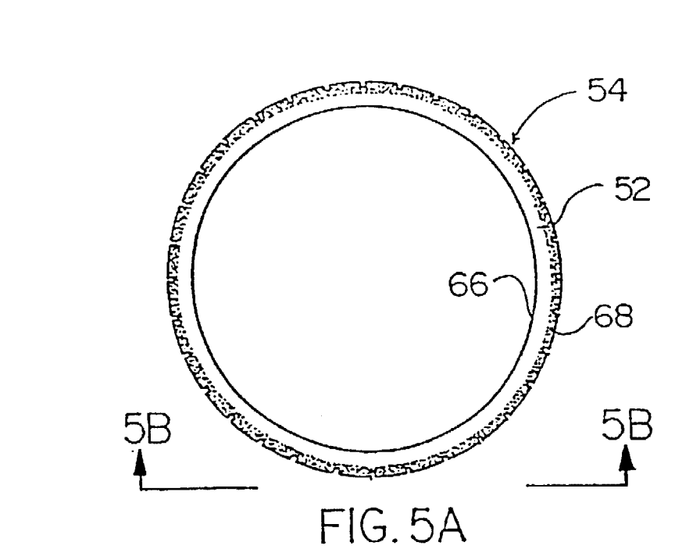
FIG. 5A is a side view of the blade of FIG. 1.
Figure 5B:
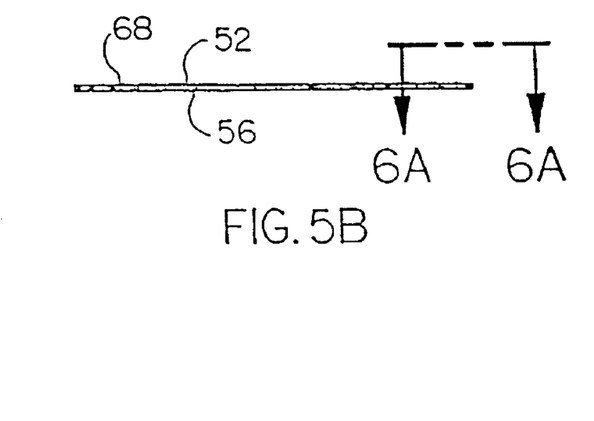
FIG. 5B is a view taken along the line 5B—5B of FIG. 5A.
Figure 6A:
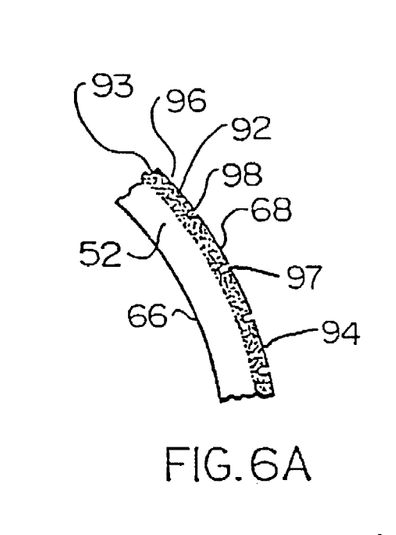
FIG. 6A is a view taken along the line 6A—6A of FIG. 5B.
Figure 6B:
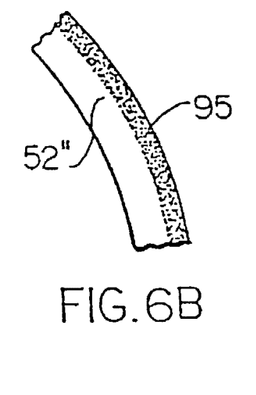
FIG. 6B is the same view as 6A, but illustrating a second type of blade.
Figure 6C:
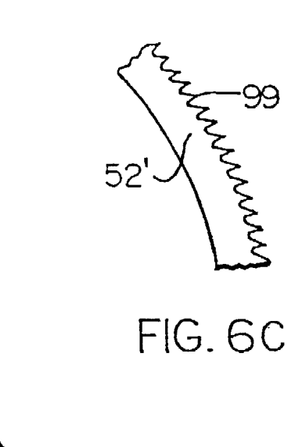
FIG. 6C is the same view as 6B but illustrating a third type of blade.

At FIGS. 5A, 5B, and 6A one can see the annular diamond (with a mesh size of 230/270) flexible blade 54 having a thickness, a diameter, a flat left face 52, which is identical to its flat right face 56, an inner edge 66, and an outer edge 68. The preferred flexible material composition of the blade 54 is type 304 stainless steel fully hardened. Cutting teeth are formed at the outer edge 68. FIGS. 6B and 6C show examples of two alternative types of blades that could be used in the saw 20 instead of the blade 54 shown in FIGS. 5A, 5B, and 6A. The rate at which the blade 54 is driven is preferably a high speed, namely on the order of 5,000 revolutions per minute. The flanged bearings 60, 64, shown in FIG. 1, rotate as the blade rotates. Each flanged bearing 60, 64 has a reentrant part, resting against the inside diameter of the inner edge 66 of the blade 54, and two flanges touching the left face 52 and right face 56 of the blade 54, respectively. The portions of the flanged bearings 60, 64 which touch the faces and the edge of the blade 54 are preferably lined with Teflon™.

The ratio of the thickness of the blade 54 relative to the outside diameter of the blade is preferably from 0.0005 to 0.005, with a typical thickness of an annular diamond flexible blade being 0.004", and a typical diameter being 3.00", which is a ratio of 0.00133. The blade 54 has an outside diameter at the outer edge 68 and an inside diameter at the inner edge 66, the flat face 52 having a width equal to half of the difference between the outside diameter and the inside diameter. The inside diameter preferably is no less than 75% of the outside diameter and no more than 95% of the outside diameter.

A broken-away portion of an unsegmented blade with diamond particles 95 is illustrated in FIG. 6B, the desirable particle size being 230/270 mesh in a matrix of nickel. A segmented design is preferable, such as shown in FIG. 6A, for increased cutting rates. Each rectangular segment or tooth comprises a long side 92, placed tangentially to the outer edge 68, a short side 93 placed radially, a leading edge 96, and a trailing edge 98. The trailing edge 98 shows an opening 97 of square shape, the length of the square side being half of the length of the rectangular segment short side 93.

When the saw is used to cut a workpiece, it produces dust particles, which, with the type of blade shown in FIG. 6B, tend to deposit on both faces of the blade 54. With an opening 97 between two segments 94, as shown in FIG. 6A, any dust generated during cutting tends to concentrate in the open trailing edge 98 rather than on the faces of the blade, thereby keeping the effective thickness of the blade thin, and keeping the cut thin, which is why the segmented blade is preferred. The dust which collects in the trailing edge opening 97 goes out in bursts, being vacuumed up by the vacuum tube 36. The dust enters the aspiration opening 37 of the vacuum tube 36, which is adjacent to the blade 54, and passes on to a vacuum outlet 112, shown in FIG. 7A. There are preferably thirty-two segments 94 in the blade 54.

At FIG. 6C, one can see a portion of an annular flexible blade carrying saw teeth 99, without a diamond surface. This type of blade can also be used.

Figure 7A:
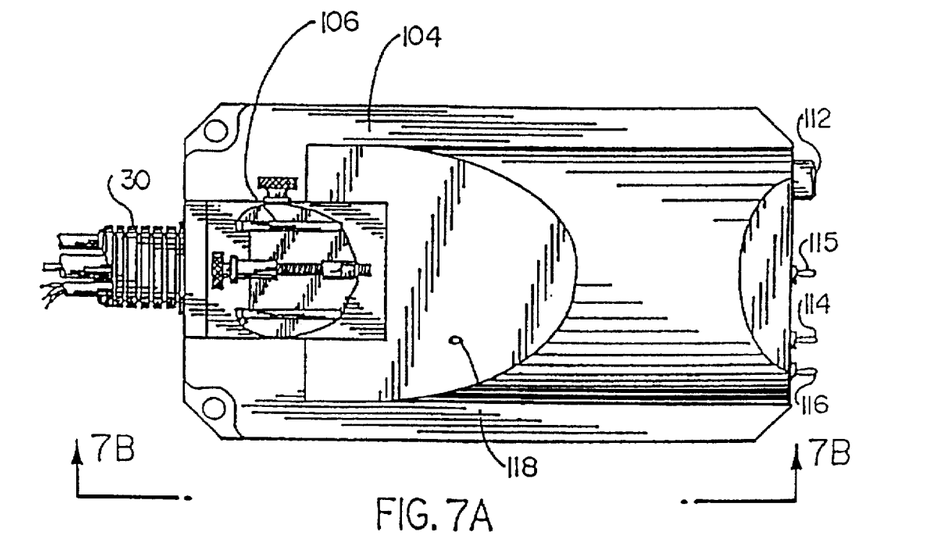
FIG. 7A is a top view of the work station which drives the saw of FIG. 1.

At FIG. 7A one can see a work station 104, which includes the motor 46 (shown in FIG. 7B), which drives the saw. The work station 104 carries a survey model table 106 and clamp, for holding the workpiece to be cut. The work station 104 also includes a vacuum outlet 112, for discharging the dust from the vacuum tube 36, a hand/foot optional selector switch 114, a foot switch connector 115, an on/off power switch 116 and an on/off light 118.

Figure 7B:
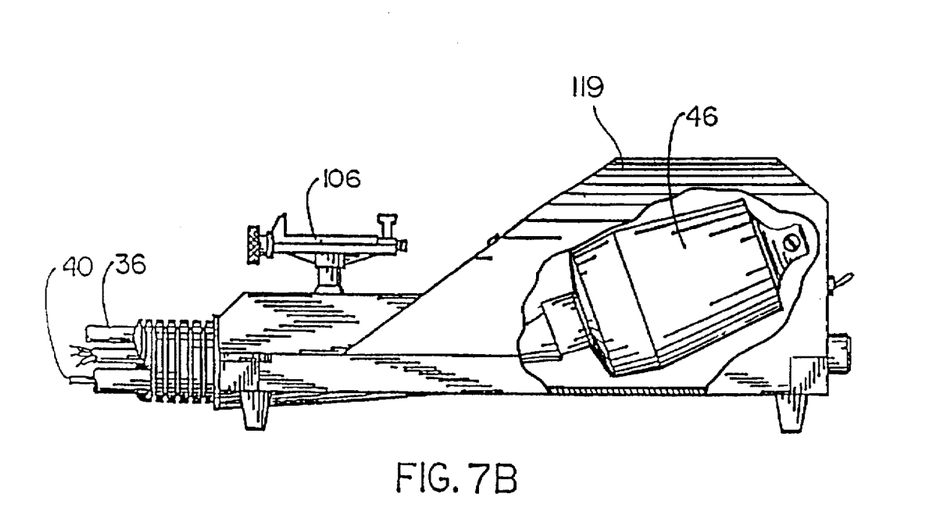
FIG. 7B is a view taken along the line 7B—7B of FIG. 7A.
Figure 8:
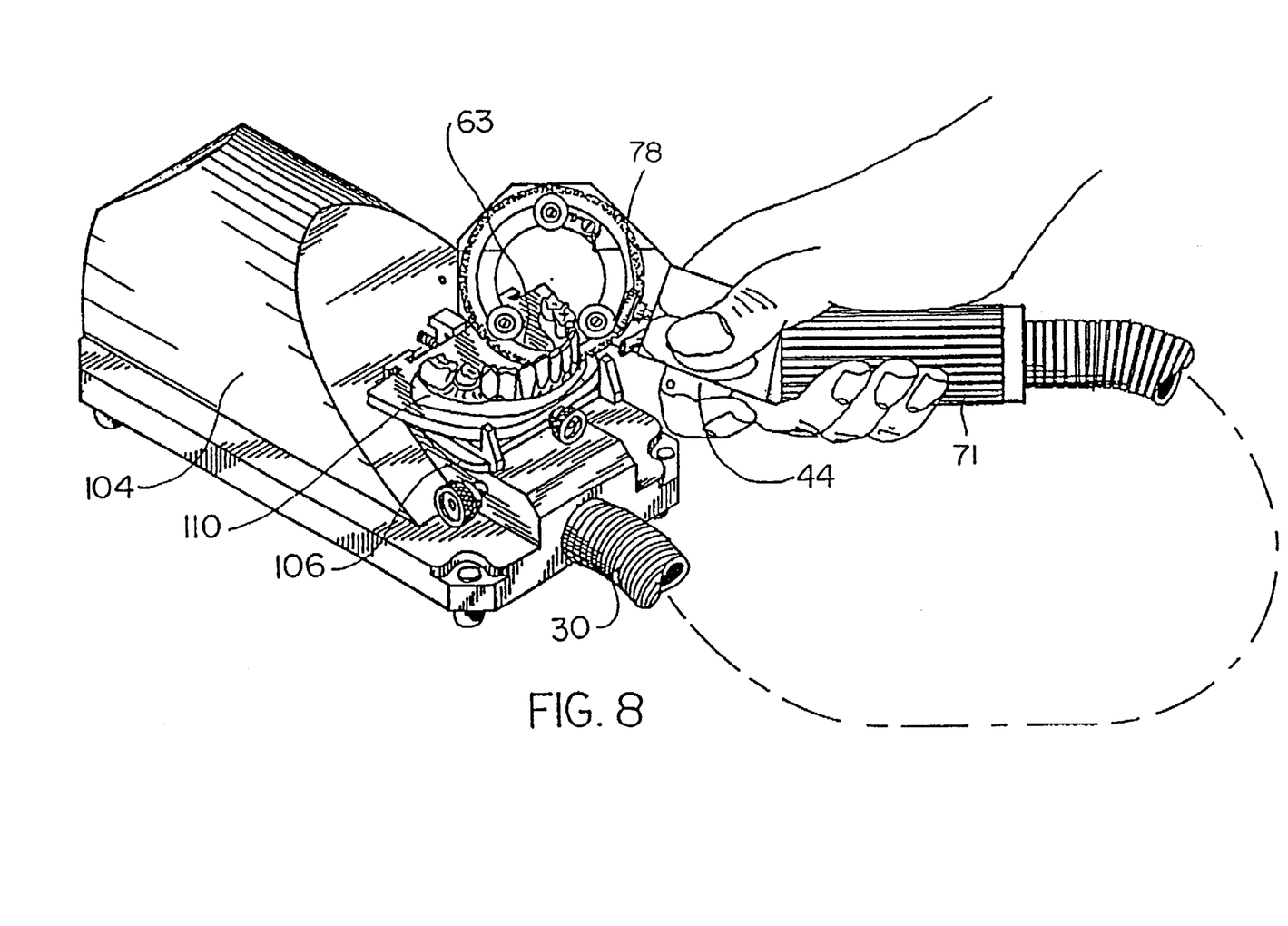
FIG. 8 is a perspective view illustrating the saw of FIG. 1 in a cutting operation.

FIG. 7B shows the motor 46 inside a fire retardant plastic cover 119 of the work station 104.

FIG. 8 shows the work station 104, the survey model table 106 and a model on which can be observed the separating of a die 110 being worked on utilizing cutting area 63.

Figure 9A:
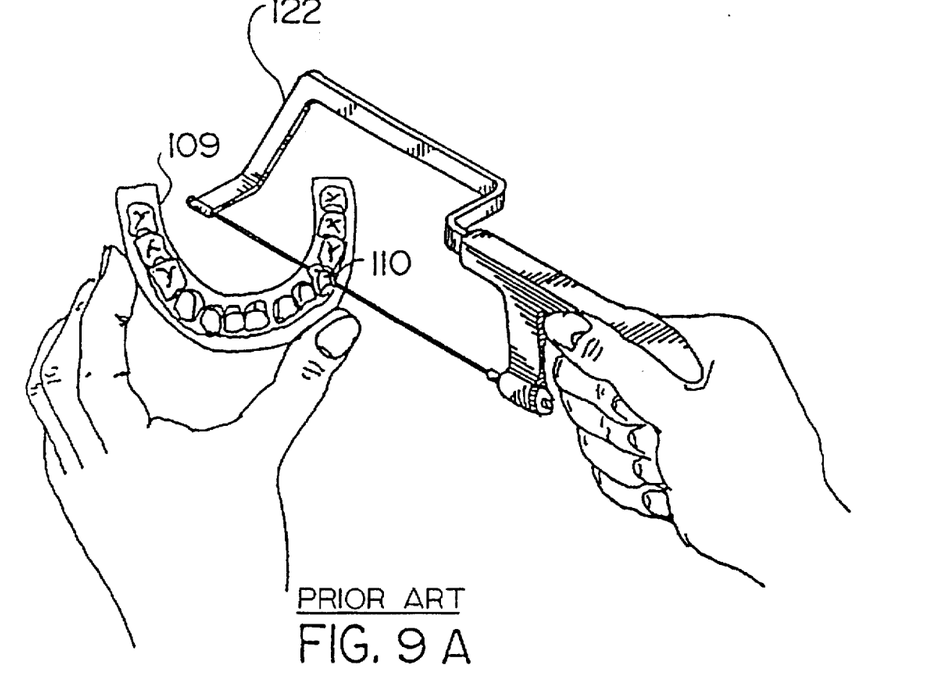
FIG. 9A is a view illustrating a cutting operation with a coping saw made in accordance with the prior art.

At FIG. 9A, one can see a view of a prior art saw. In that view, a model 109 is shown being held by hand, and a traditional coping saw is being used to separate the die.

Figure 9B:
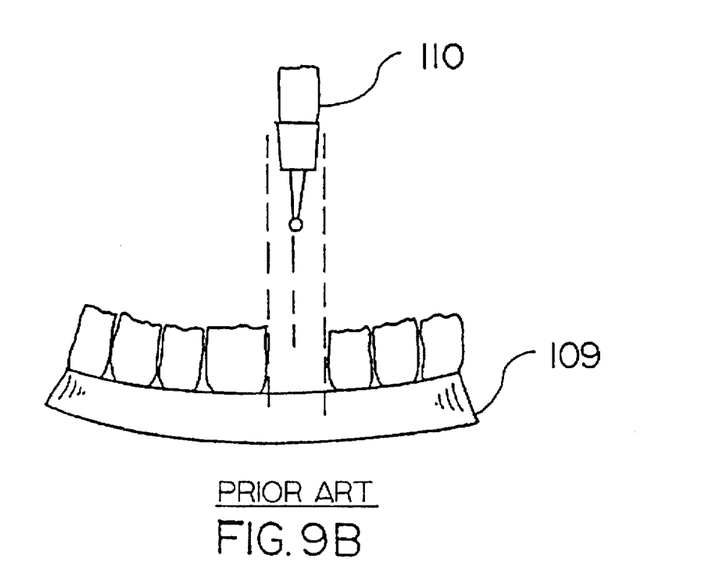
FIG. 9B is a view of a dental model with the die extracted.

At FIG. 9B one can see a die 110 extracted from the model 109 once the cuts have been made on each side.

Figure 10:
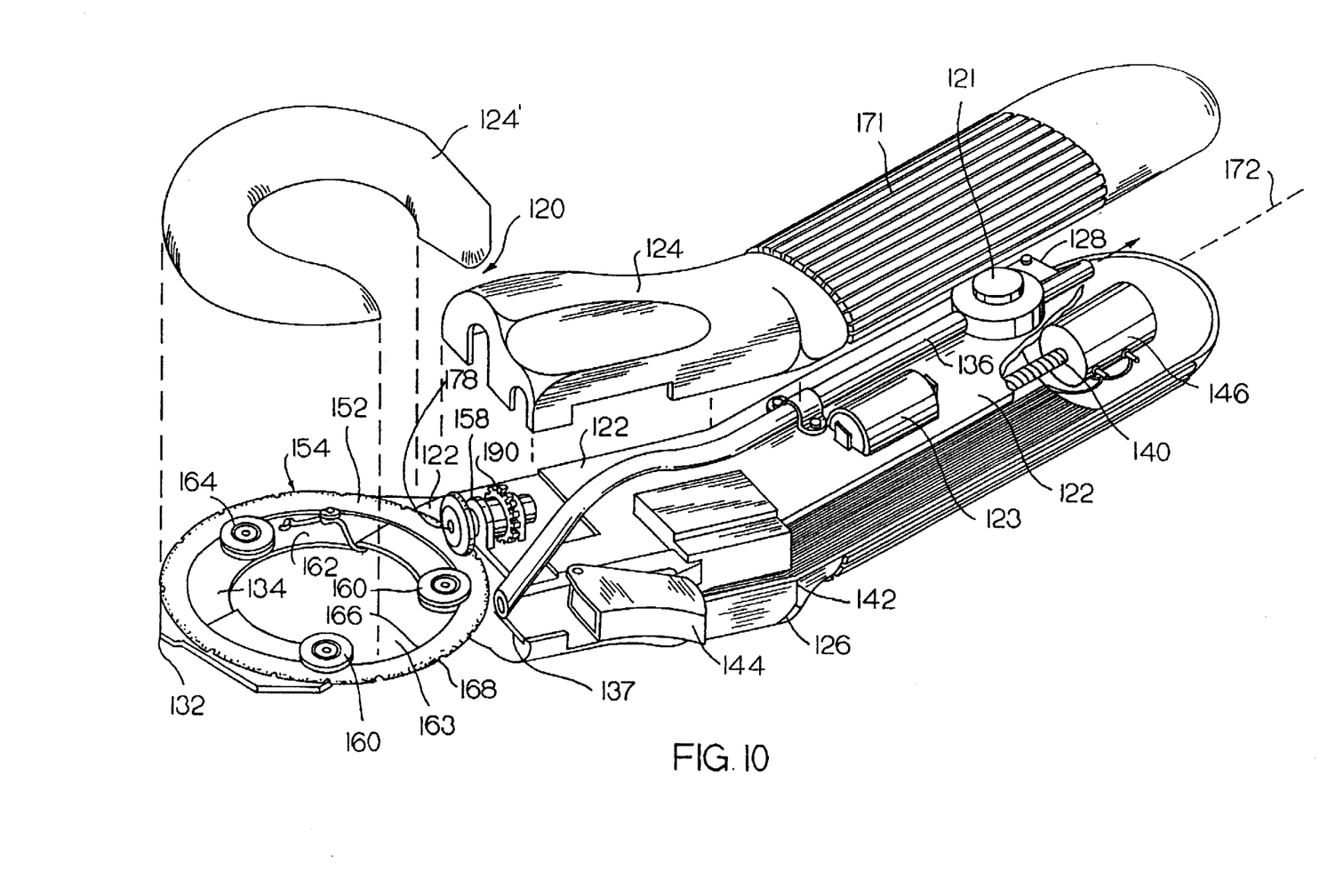
FIG. 10 is an exploded perspective view of a second embodiment of a saw made in accordance with the present invention.

FIG. 10 shows a second embodiment of a saw made in accordance with the present invention. The parts of this second embodiment are numbered the same as the comparable parts in the first embodiment, except that the numbers are preceded by a "1". The saw 120 of FIG. 10 is the same as the saw 20 shown in the previous figures, except that, instead of being driven by a remote motor and having a remote vacuum line coming to the saw through a cable, in this embodiment, there is a small, battery-powered direct current motor 146 located in the handle of the saw itself. The motor 146 drives a drive cable 140, which drives the gear 148 (not shown), which drives the opposite gear 190. The drive cable 140 also drives the drive wheel 150 (not shown) and the follower wheel 178, as in the first embodiment. There is also a small vacuum unit 121 located in the handle, which pulls a vacuum through the vacuum tube 136, so that particles are pulled into the tube 136 through the aspiration opening 137, as in the previous embodiment.

There is a rechargeable battery pack 123 in the handle, and the saw 120 can be plugged into an electrical outlet to recharge the battery 123 between uses. There is an on-off switch (not shown) on the saw 120, which turns on the vacuum unit 121. The battery 123 drives the motor 146 and the vacuum unit 121.

As with the first embodiment, this embodiment includes a main body 122, a left shell 124, right shell 126, aft end 128, fore end 132, arched support 134, and a variable speed control 142, which controls the speed of the motor 146 in response to the finger plunger 144. The drive cable 140 drives the gear (directly opposite the gear 190), drive wheel (directly opposite the follower wheel 178), and the blade 154. FIG. 10 shows the left face 152 of the blade 154, which is a mirror image of the right face of the blade (not shown in this FIG.). There is a drive assembly 158, which is the same as the drive assembly 58 in the first embodiment. There are also fixed guide bearings 160, a cutting area 163, a movable flanged guide bearing 164, and an inner edge 166 and an outer edge 168 of the blade 154. This embodiment also includes a grip 171, having an axis 172, which is the same as the grip axis 72 of the first embodiment, and that grip axis 172 is also tangent to the outer edge 168 of the blade in the cutting portion 163 of the blade 154.

MODE OF OPERATION

The first step is to secure the workpiece which is to be cut. To secure a dental model, the model is clamped on the survey model table 106, as shown in FIG. 8. If the saw is to be used to cut a different type of workpiece, then that workpiece must also be secured in some manner.

In dentistry, the model is first placed on the survey table 106. Then, the operator holds the saw 20 by the grip 71 and places the cutting area 63 of the saw 20 above the area of the workpiece to be cut. The operator slowly depresses the finger plunger 44 to control the cutting speed. The operator may increase or decrease the speed as the cut progresses. The operator can start the cut from the top towards the bottom, as would be done with a coping saw, and he can also change the direction of the cut when needed, because of the flexibility of the blade and the fact that the axis of rotation of the handle is tangent to the outer edge of the blade. The dust produced by the cutting action is sucked away through the aspiration opening 37, which is connected to a vacuum outlet 112. The vacuum outlet 112 may be connected to an existing vacuum system in the laboratory.

The only difference between the embodiment of FIG. 10 and the embodiment of FIG. 1 in terms of function is that the FIG. 10 embodiment is not tied to a remote motor and vacuum unit by a cable and can, therefore, be freely movable.

TECHNOLOGICAL ADVANCEMENTS

A useful feature of the annular diamond flexible blade held by the saw is its ability to reproduce, in a motorized saw, at nearly 100% success rate, a function which could only be performed by a manual coping saw prior to the present invention. The motorized annular saw of the present invention allows the operator to change directions during the cutting function. Known motorized saws do not permit the operator to perform this function.

In addition, most prior art motorized saws are limited to a fixed direction of cut; the operator must first align the die at right angles to the saw before proceeding with the desired cut. Once this is performed, the operator then either brings the die up to the cutting blade or vice-versa to perform the first task.

The deficiency of the prior art motorized saws is evident when an operator attempts to perform a second cut, which must be aligned either parallel to or at an inverted taper with the first cut. This task becomes very difficult, time consuming, and lacks precision. The only alternative which is presently available to the operator is to return to the hand held coping saw in order to attain the desired level of precision and/or finish the cut.

The present invention corrects this deficiency. First, greater maneuverability is achieved. Second, the variable speed which is available permits the operator to start the cut slowly with great precision during the more difficult and delicate initial cut and to then speed up to complete the cut. Third, it completely eliminates the need for the use of the hand held coping saw. The flanged guide bearings 60, 64, the drive wheel 50, and the follower wheel 78 are localized at a certain distance from the work zone to permit a flexing of the blade to occur during the cutting operation, as the cutting part of the blade is remote from the zone of the application of friction by the wheels 50 and 78.

Over the years, manufacturers have developed synthetic stone material for producing dental dies with greater accuracy and increased wear resistance. As the stones have become harder, it has become more difficult for coping saw blades to make the cut, and the blades often break. It is time consuming and expensive to replace them. The present invention provides blades with much longer life, thereby saving substantial time.

Another major deficiency with present fixed motorized blades is the fact that some of the models have a high level of vibration. This causes the cuts to lack precision, but, more importantly, it often causes the die itself to crack or break. If this happens, the whole process must be started again, and a new imprint of the client's teeth must be made in order to prepare a new die. This is both time consuming and expensive. The present invention alleviates this problem, since the vibration will be negligible, and by the fact that the operator can adjust the speed of operation, depending on the level of difficulty and precision which is associated with the cut. The present invention will also introduce a new level of precision to the cutting process because of the thinness of the blades. The thinner blade will cause the operator to achieve a higher level of precision, will minimize the vibration, and will also lower the risk of damaging the dental imprint reproduction.

It is well understood that modifications may be made to the embodiments described above without departing from the scope of the present invention.

What is claimed is:

1. A saw, comprising:
    a grip, having a substantially cylindrical portion defining an axis of rotation;
    an annular flexible blade having
        first and second opposed flat faces;
        a thickness defined by the distance between said flat faces;
        an outer edge; and
        an inner edge; said outer edge being a cutting edge, with the axis of rotation of the grip being tangent to said cutting edge; and
    a drive for driving said blade, including a drive wheel, which contacts one of said flat faces of said blade.

2. A saw as recited in claim 1, wherein said drive includes a motor carried on the saw; and wherein said motor drives said drive wheel.

3. A saw as recited in claim 2, and further including a battery, carried on said saw, said battery providing power to said motor.

4. A saw as recited in claim 3, wherein the battery is rechargeable.

5. A saw, comprising:
    a grip, defining an axis;
    an annular flexible blade having
        first and second opposed flat faces;
        a thickness defined by the distance between said flat faces;
        an outer edge; and
        an inner edge; said outer edge being a cutting edge: and
    a drive for driving said blade, including a drive wheel, which contacts one of said flat faces of said blade;
    wherein said drive further includes a drive cable, which extends through said handle; a follower wheel, which is also driven by said drive cable and which contacts the other of the flat faces; and a motor, which drives said drive cable, said motor being remote from said grip.

6. A saw as recited in claim 5, and further comprising a vacuum tube extending through said grip and terminating adjacent to said cutting edge in order to vacuum up dust particles that are formed when the saw cuts a workpiece.

7. A saw as recited in claim 6,
    and further comprising a motor mounted on said saw and connected to said drive cable; and a vacuum unit mounted on said saw and connected to said vacuum tube.

8. A saw as recited in claim 5, and further comprising a work station, at which is located said motor; said work station also including a survey model table for holding a workpiece to be cut by the saw.

9. A saw as recited in claim 5, and further comprising an on-off switch at said remote motor.

10. A saw, comprising:
    a grip, defining an axis;
    an annular flexible blade having
        first and second opposed flat faces;
        a thickness defined by the distance between said flat faces;
        an outer edge; and
        an inner edge; said outer edge being a cutting edge; and
    a drive for driving said blade, including a drive wheel, which contacts one of said flat faces of said blade;
    wherein the outer edge of said blade defines an outside diameter, the inner edge of said blade defines an inside diameter, and said inside diameter is no less than 75% and no more than 97% of said outside diameter.

11. A saw as recited in claim 10, wherein the ratio of the thickness of said blade to the outside diameter of said blade is from 0.0005 to 0.005.

12. A saw, comprising:
    a grip, defining an axis;
    an annular flexible blade having first and second opposed flat faces, an outer edge, and an inner edge; said outer edge being a cutting edge;
    a drive wheel in contact with one of said flat faces for driving said blade;
    a drive cable extending through said grip; wherein said drive cable drives said drive wheel; and
    a vacuum tube extending through said grip and terminating adjacent to said blade for vacuuming up dust particles formed as the saw cuts a workpiece;
    and further comprising a motor unit, remote from said saw; and a flexible cable connecting said motor unit to said saw; wherein said drive cable is driven by said motor and extends through said flexible cable; and wherein said vacuum tube extends through said flexible cable.

13. A saw as recited in claim 12, wherein the axis of said grip is tangent to said cutting edge.

14. A saw as recited in claim 12, and further comprising electrical wiring extending from said motor unit to said saw through said flexible cable.

* * * * *